(12) United States Patent
Taylor et al.

(10) Patent No.: US 8,863,781 B2
(45) Date of Patent: Oct. 21, 2014

(54) CONSTRICTING PRESSURE VALVE APPARATUS AND METHODS THEREOF

(75) Inventors: Jon B. Taylor, Groton, MA (US); James J. Kennedy, III, Candia, NH (US); Paul LaRue, Chesterfield, NH (US); George P. Hannafin, Hudson, NH (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 148 days.

(21) Appl. No.: 13/416,222

(22) Filed: Mar. 9, 2012

(65) Prior Publication Data

US 2013/0236354 A1      Sep. 12, 2013

(51) Int. Cl.
*F16K 15/14*     (2006.01)

(52) U.S. Cl.
USPC .............. 137/843; 137/529; 137/852

(58) Field of Classification Search
CPC . F16K 15/141; F16K 15/148; F16K 17/0453; A61L 2/26
USPC .............. 137/843, 852, 854, 528, 535, 512.5, 137/223, 225, 529; 251/331, 358; 422/295
See application file for complete search history.

(56) References Cited

U.S. PATENT DOCUMENTS

| | | | |
|---|---|---|---|
| 4,381,019 A * | 4/1983 | Lindtveit | .............. 137/843 |
| 4,748,003 A | 5/1988 | Riley | |
| 5,019,345 A | 5/1991 | Lorenz | |
| 5,097,865 A | 3/1992 | Riley | |
| 6,317,477 B1 | 11/2001 | Matteson | |
| 2003/0091471 A1 | 5/2003 | Lacabanne | |
| 2005/0238530 A1 | 10/2005 | Frieze et al. | |

* cited by examiner

*Primary Examiner* — Kevin Lee
*Assistant Examiner* — P. Macade Nichols
(74) *Attorney, Agent, or Firm* — Hayes Soloway P.C.

(57) ABSTRACT

A valve apparatus and methods associated thereof are provided. The valve apparatus includes a valve housing structure. A first valve portion is connected to the valve housing structure, wherein the first valve portion has a sealing edge. A second valve portion is positioned at least partially within the valve housing structure. A constrictable membrane has a pressurizable interior compartment, wherein the constrictable membrane supported by the second valve portion and positioned proximate to the first valve portion, wherein at least a portion of the constrictable membrane is movable to engageable with the sealing edge of the first valve portion.

12 Claims, 6 Drawing Sheets

CONSTRICTING PRESSURE VALVE APPARATUS AND METHODS THEREOF

FIELD OF THE DISCLOSURE

The present disclosure is generally related to valves and more particularly is related to a constricting pressure valve apparatus for use with a medical sterilization container.

BACKGROUND OF THE DISCLOSURE

Articles such as medical instruments and the like are usually sterilized in an autoclave in which the articles are exposed to high-pressure saturated steam for a relatively brief interval. Unless the articles are to be used immediately and in close proximity to the autoclave, it is desirable to sterilize the articles while they are inside a valved container as described, for example, in U.S. Pat. No. 4,748,003. During the sterilization process, the valves open under the influence of high pressure steam in the autoclave exposing the contents of the container to the hot steam. At the end of the sterilization cycle, when the pressure in the autoclave outside the container is returned to normal, i.e. atmospheric pressure, the valves close so that when the container is removed from the autoclave, the now sterilized articles are maintained in a completely sealed sterile environment until they are needed.

The sterilization container described in the above patent has pressure-actuated valves in the top and bottom walls of the sterilization container. Each valve has a large valve opening and a closure therefor, the latter being supported by a bellows capsule mounted inside the container. A return spring mechanism normally maintains the valve closure in its closed position. However, when the pressure outside the container exceeds that within the container by a few pounds per square inch, the force on the valve closure exceeds that exerted by the return spring with the result that the valve closure opens sufficiently to allow high-pressure steam to enter the container. That steam collapses the bellows, which thereupon moves the valve closure to its fully open position. Both valves being open, high-pressure steam can sweep through the container and sterilize the articles therein. When the pressure inside the autoclave returns to normal after completion of the sterilization cycle, the return spring moves the valve closure of each valve to its closed position thereby sealing the container. As also described in that patent, pressure equalization occurs through a special filter member mounted in the container wall so that a sterile environment at ambient pressure is maintained in the container until the container is opened to remove the articles therefrom.

While the valve described in the above patent operates satisfactorily, it does have certain to drawbacks. First and foremost, the bellows capsule has a relatively small diameter in relation to the valve opening and a large length-to-diameter ratio, e.g. 1.3 in./1 in.=1.3. This means that when the valve member starts to open in response to a given pressure differential outside and inside the container and the bellows is collapsed lengthwise, there is a relatively large reduction in the volume of the bellows, i.e. in excess of 20%, and a correspondingly large increase in gas pressure inside the bellows which resists further opening of the valve member. To avoid this problem, the bellows capsule in the prior value has to be evacuated. This necessitates the use of an elaborate return spring mechanism in order to overcome the increased back pressure and close the valve. Also, the requirement for a bellows that must be evacuated makes the valve somewhat more difficult and expensive to manufacture. In addition, sometimes a small leak may develop in the bellows so that air enters the bellows. Resultantly, during the next sterilization cycle, when the valve member begins to open, that air will be compressed, effectively increasing the spring constant of the bellows so that the valve member does not open as much for a given pressure differential outside and inside the container.

Thus, a heretofore unaddressed need exists in the industry to address the aforementioned deficiencies and inadequacies.

SUMMARY OF THE DISCLOSURE

Embodiments of the present disclosure provide a valve apparatus. Briefly described, in architecture, one embodiment of the apparatus, among others, can be implemented as follows. The valve apparatus includes a valve housing structure. A first valve portion is connected to the valve housing structure, wherein the first valve portion has a sealing edge. A second valve portion is positioned at least partially within the valve housing structure. A constrictable membrane has a pressurizable interior compartment, wherein the constrictable membrane supported by the second valve portion and positioned proximate to the first valve portion, wherein at least a portion of the constrictable membrane is movable to engageable with the sealing edge of the first valve portion.

The present disclosure can also be viewed as providing systems for sterilizing medical instruments. Briefly described, in architecture, one embodiment of the system, among others, can be implemented as follows. The system for sterilizing medical instruments includes a sterilization container having a plurality of walls, a base, and a top, wherein at least a portion of the plurality of walls, the base, and the top substantially enclose the sterilization container. A valve housing structure is positioned within at least one of the plurality of walls, the base, and the top. A first valve portion is connected to the valve housing structure, wherein the first valve portion has a sealing edge. A second valve portion is positioned at least partially within the valve housing structure. A constrictable membrane has a pressurizable interior compartment, wherein the constrictable membrane supported by the second valve portion and positioned proximate to the first valve portion, wherein at least a portion of the constrictable membrane is movable to engageable with the sealing edge of the first valve portion.

The present disclosure can also be viewed as providing methods of sterilizing a medical instrument. In this regard, one embodiment of such a method, among others, can be broadly summarized by the following steps: placing a sterilization container having the medical instrument positioned therein within a sterilization environment; heating the sterilization environment, thereby opening a constricting valve positioned within the sterilization container; transferring a sterilant through the constricting valve to sterilize the medical instrument positioned within the sterilization container; after the medical instrument is sterilized, decreasing a temperature of the sterilization environment to close the constricting valve, whereby the closed constricting valve seals the sterilization container and prevents a biological contaminant from accessing the medical instrument therein; and removing the sterilization container from the sterilization environment.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
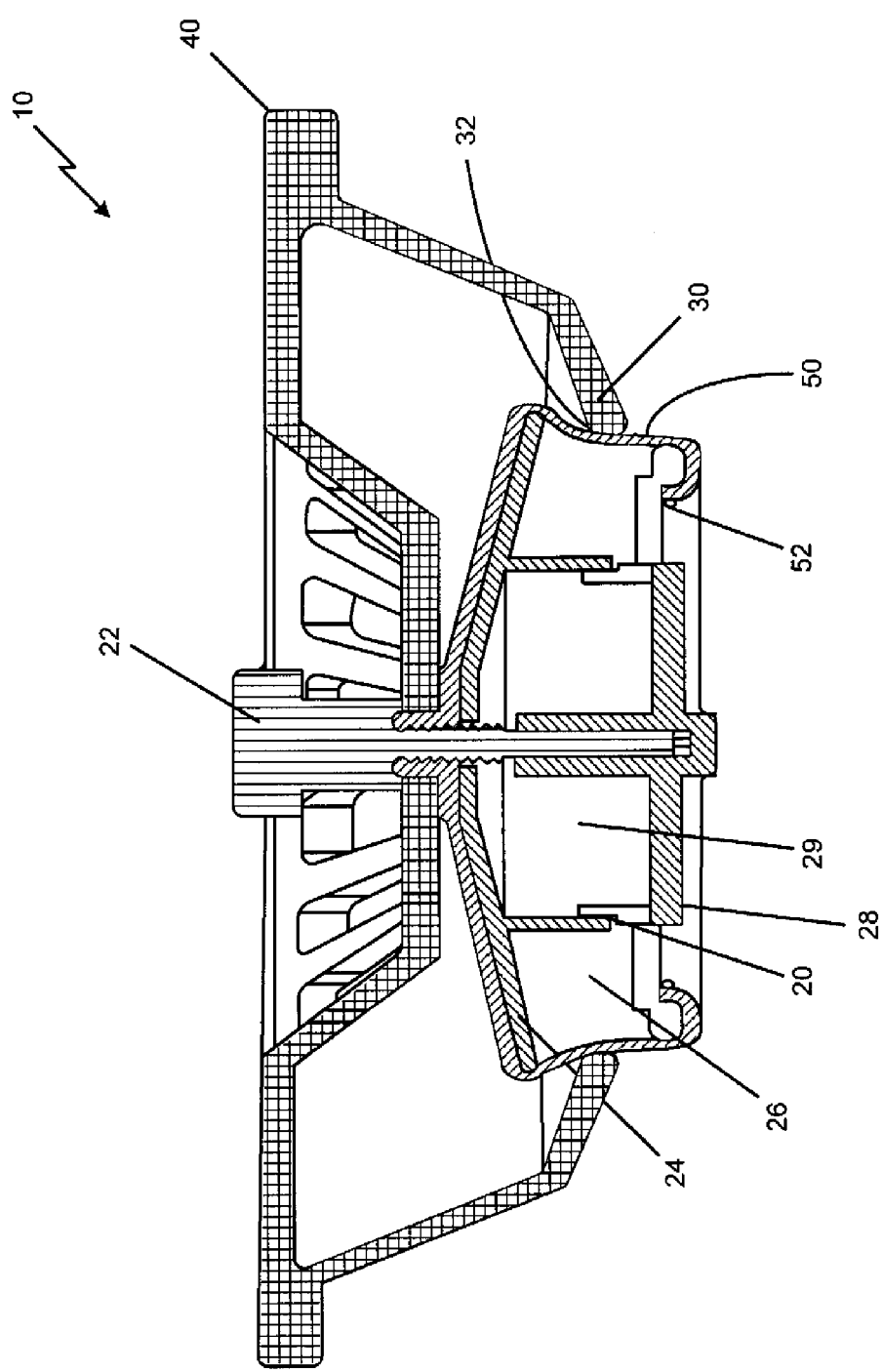
FIG. 1 is a cross-sectional illustration of a valve apparatus, in accordance with a first exemplary embodiment of the present disclosure.

FIG. 1 is a cross-sectional illustration of a valve apparatus 10, in accordance with a first exemplary embodiment of the present disclosure. The valve apparatus 10, which may be referred to herein as 'apparatus 10' includes a valve housing structure 40. A first valve portion 30 is connected to the valve housing structure 40, wherein the first valve portion 30 has a sealing edge 32. A second valve portion 20 is positioned at least partially within the valve housing structure 40. A constrictable membrane 50 has a pressurizable interior compartment 29, where the constrictable membrane 50 is supported by the second valve portion 20 and positioned proximate to the first valve portion 30. At least a portion of the constrictable membrane 50 is movable to engageable with the sealing edge 32 of the first valve portion 30.

The valve apparatus 10 may include any type of valve used with any type of structure. Preferably, the valve apparatus 10 is used with a medical instrument sterilization container used to sterilize medical instruments before and after medical procedures. The valve apparatus 10, however, can be used with other structures conventionally used with a sterilization process, and/or capable of enduring a sterilization process, or structures that are not used for sterilization processes.

The valve housing structure 40 may include any device, structure, portion of a structure or combination thereof that supports or is connected to one of the first and second valve portions 30, 20. For example, the valve housing structure 40 may be integral with the first valve portion 30 and may be affixed, by any means, such as bonding, gluing and/or ultrasonic welding to the sterilization container. Alternatively, the valve housing structure 40 may be affixed with any type of fastener to the second valve portion 20. In FIG. 1, the second valve portion 20 is affixed to the valve housing structure 40 with a threaded fastener 22. As can be seen, any number or type of valve housing structures 40 may be used in any combination to secure, position or support the valve apparatus 10 to a sterilization container.

The first valve portion 30 and the second valve portion 20 may include any type of valve portions that are positioned proximate to each other. As is illustrated in FIG. 1, the first valve portion 30 is affixed to the valve housing structure 40, which may be in communication with a sterilization container. The first valve portion 30 may be permanently or removably affixed or attached to the valve housing structure 40 with any device or process. For example, as is shown in FIG. 1, the first valve portion 30 is integrally bonded with the valve housing structure 40.

The first and second valve portions 30, 20 may be characterized as any type of structures within a valve that are positioned proximate to one another. The identifications of a 'first' and/or 'second' portion are included to convey the details of the present disclosure, and should not be read to limit the scope valve apparatus 10. The first and second valve portions 30, 20 may include a variety of designs and structures, all of which are considered within the scope of the present disclosure. For example, in FIG. 1, the first valve portion 30 is positioned about the circumference of the second valve portion 20, thus positioning the sealing edge 32 circumferentially about the constrictable membrane 50. The second valve portion 20 includes an interior portion having a pressurizable interior compartment 29 defined by any part or parts of the second valve portion 20 and/or the constrictable membrane 50. The pressurizable interior compartment 29 may be capable of holding a pressurized atmosphere, such as an atmospheric pressure of approximately 14.7 pounds per square inch (psi). The pressurized interior compartment 29 may be formed from any combination of the structure of the second valve portion 20 and the constrictable membrane 50.

The constrictable membrane 50 may include any type of membrane, flexible material, substantially flexible material and/or any other device or material capable of constricting. For example, the constrictable membrane 50 may include a rubber material and/or a silicone material that is able to flex, bend and move. The constrictable membrane 50 may be attached to at least a portion of the second valve portion 20, wherein the constrictable membrane 50 is positioned on an exterior surface of the second valve portion 20, such as by stretching the constrictable membrane 50 over the exterior surface. In accordance with this disclosure, a constrictable membrane 50 attached to the second valve portion 20 may include a constrictable membrane 50 that is integral with, bonded to, coupled to, fastened to and/or engaged with any part of the first valve portion. In FIG. 1, the constrictable membrane 50 is illustrated as covering an upper valve part 24, an open sidewall 26 and a portion of the bottom valve part 28 of the second valve portion 20. The upper and lower valve parts 24, 28 may be affixed to the valve housing with the threaded fastener 22, or another structure. The constrictable membrane 50 may be affixed to the second valve portion 20 by any type of attachment device 52 or attachment method. This may include a device and/or any bonding or adhesive process that retains the constrictable membrane 50 securely.

As is illustrated in FIG. 1, the constrictable membrane 50 may be positioned over an open sidewall 26 of the second valve portion 20. The open sidewall 26 may be characterized as a gap between the upper and bottom valve parts 24, 28 of the second valve portion 20. In this position, the constrictable membrane 50 may contact and engage a sealing edge 32 of the first valve portion 30, which may create a seal or sealed junction between the constrictable membrane 50 and the first valve portion 30. The sealing edge 32 of the first valve portion 30 may be positioned between the upper and bottom valve parts 24, 28 of the second valve portion 20, to position the sealing edge 32 appropriately for contact with the constrictable membrane 50. This seal between the sealing edge 32 and the constrictable membrane 50 may be capable of preventing the flow of a sterilization material and/or gas from traversing through the valve apparatus 10. Accordingly, when the constrictable membrane 50 is engaged with the first valve portion 30, any interior portion (not shown) of the sterilization container may be sealed off from substances or an atmosphere exterior to the sterilization container.

Figure 2:
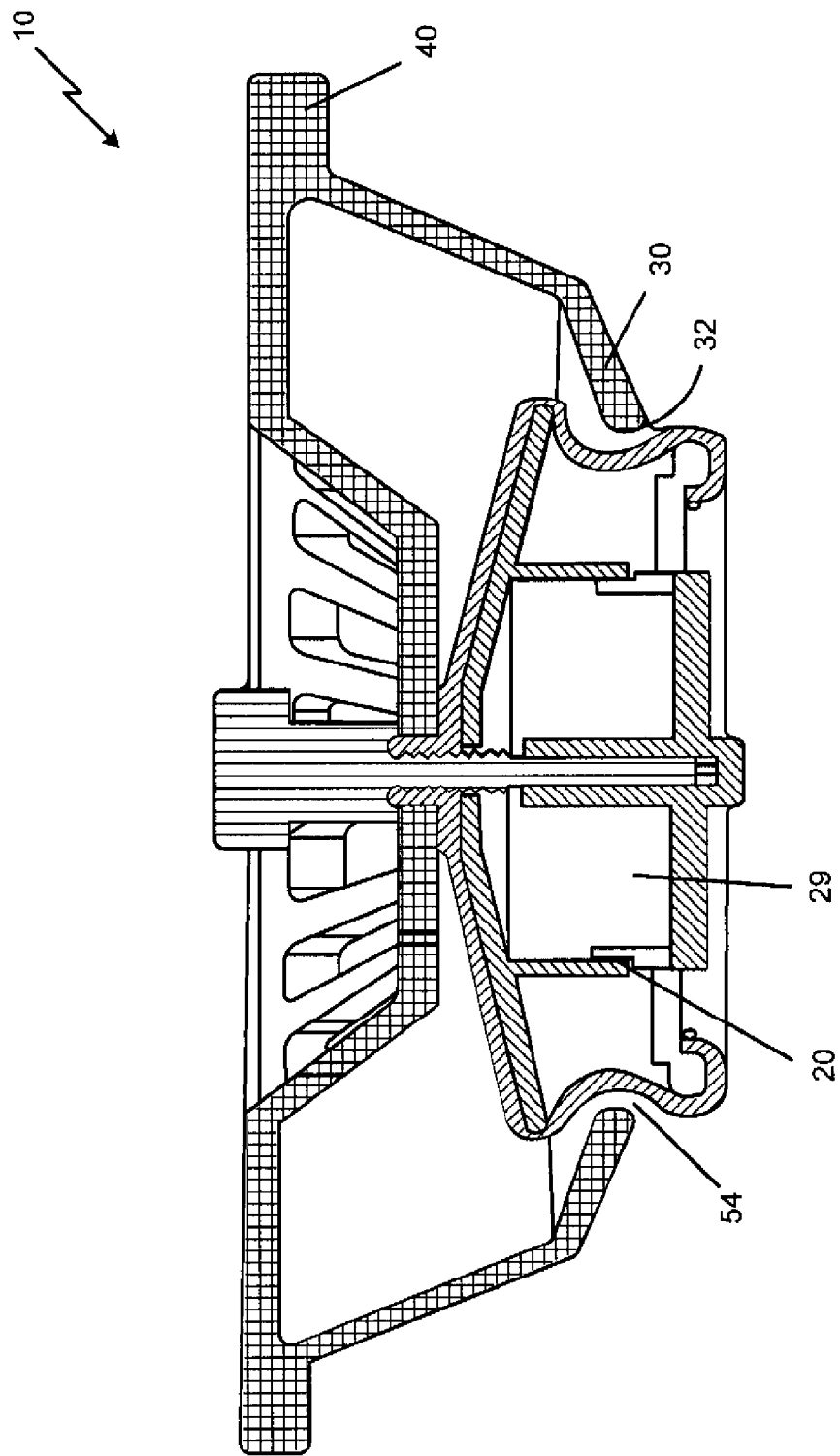
FIG. 2 is a cross-sectional illustration of a valve apparatus of FIG. 1 in a non-engaged position, in accordance with the first exemplary embodiment of the present disclosure.

FIG. 2 is a cross-sectional illustration of a valve apparatus 10 of FIG. 1 in a non-engaged position, in accordance with a first exemplary embodiment of the present disclosure. In other words, FIG. 2 illustrates the valve apparatus 10 in the open position, whereas FIG. 1 illustrates the valve apparatus 10 in the closed position, as discussed above. As can be seen in FIG. 2, the constrictable membrane 50 may be in the non-engaged or non-contacting position when it is positioned to create a void 54 between the constrictable membrane 50 and the first valve portion 30 to allow the flow of gasses and/or sterilant through the valve apparatus 10. The valve apparatus 10 may function by allowing the transmission of a sterilization material, a gas, a liquid and/or a pressurized atmosphere from one side of the valve apparatus 10 to the other side. The void 54 may permit the sterilization material, gas, liquid and/or pressurized atmosphere to traverse through the valve apparatus 10. Thus, the first and second valve portions 30, 20 may remain in substantially constant relative positions to one another while the constrictable membrane 50 is flexed between positions.

Movement between the closed position shown in FIG. 1 and the open position shown in FIG. 2 may occur through the application of pressure to and/or within the sterilization container. Pressure may be applied in any pressurized environment, such as an autoclave chamber used to create high pressure and high heat for a sterilization process, relative to an ambient heat and pressure external to the autoclave chamber. For example, the sterilization container with valve apparatus 10 may be placed within an autoclave chamber. When the pressure within the autoclave chamber is substantially equal to that outside the autoclave chamber, the constrictable membrane 50 may remain in the closed/engaged position. When the pressure in the autoclave chamber increases, such as from the application of heat in a sterilization process, the constrictable membrane 50 may be forced to move from the closed/engaged position to the open/non-engaged position. This movement of the constrictable membrane 50 is due to the pressure within the interior portion of the second valve portion 20 remaining at an atmospheric pressure of approximately 14.7 psi, while the pressure within the autoclave chamber increases above the atmospheric pressure. For example, the pressure within the autoclave chamber may increase up to approximately 42 psi. Thus, as the pressure within the autoclave chamber is adjusted, the position of the constrictable membrane 50 between a fully closed, fully engaged position with the first valve portion 30 and an open, non-engaged position with the first valve portion 30 may be achieved.

Figure 3:
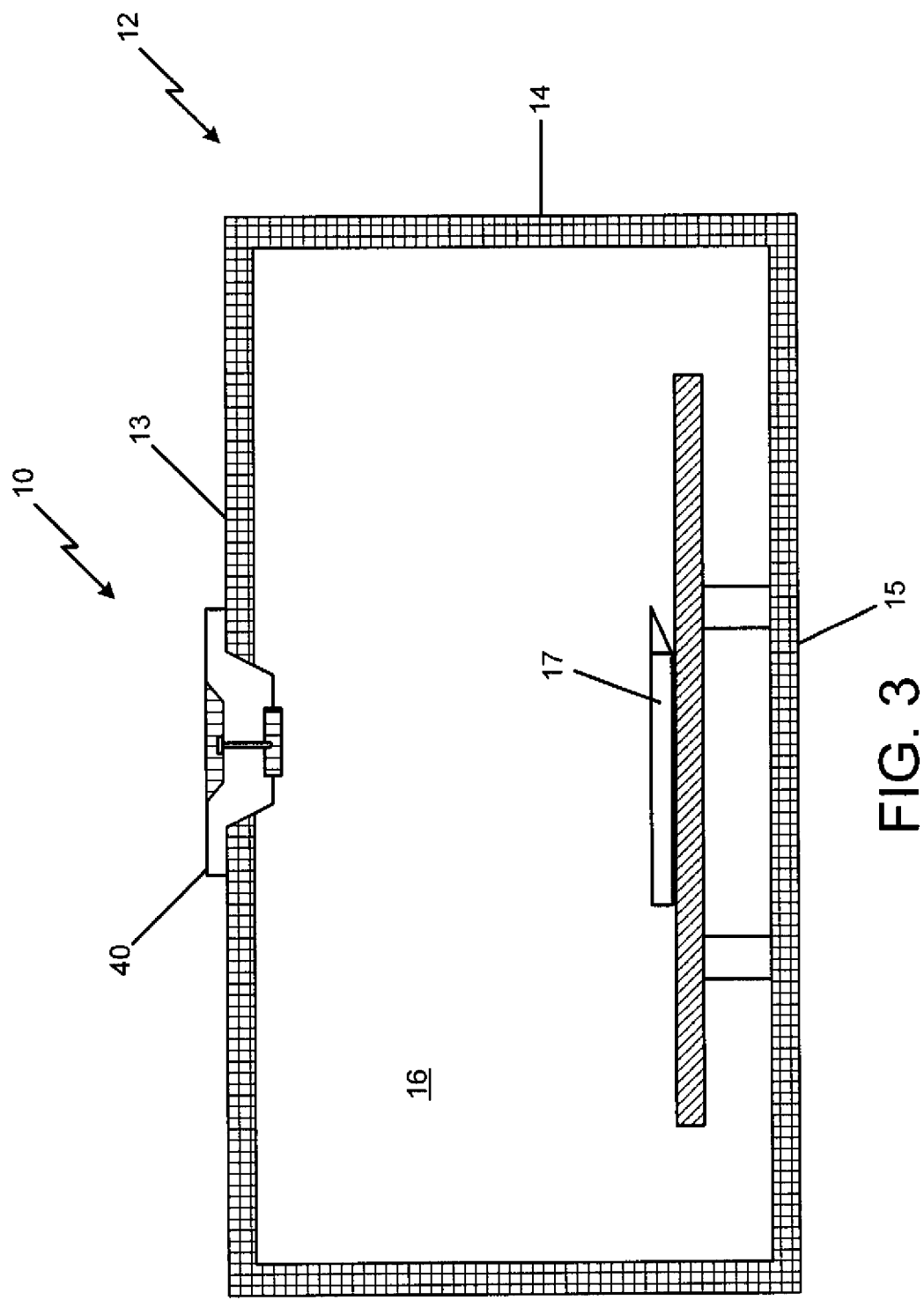
FIG. 3 is a cross-sectional illustration of a valve apparatus within a sterilization container, in accordance with the first exemplary embodiment of the present disclosure.

FIG. 3 is a cross-sectional illustration of a valve apparatus 10 within a sterilization container 12, in accordance with the first exemplary embodiment of the present disclosure. As is shown in FIG. 3, the valve apparatus 10 is positioned within a wall of the sterilization container 12. The valve housing structure 40 of the valve apparatus 10 may be positioned within one or more of the top 13, the base 15, and/or one of the sidewall 14 of a sterilization container 12. Preferably, the valve apparatus 10 will be positioned within the top 13 of the sterilization container 12 to allow for easy access to the valve apparatus 10 by a medical practitioner and to provide unobstructed access of a sterilant to the valve apparatus 10. The valve apparatus 10 may be positioned between an exterior atmosphere of the sterilization container 12 and an interior area 16 of the sterilization container 12 where one or more medical instruments 17 are housed. As was discussed previously, the sterilization container 12 may be used to sterilize a variety of medical tools and devices to make them safe for use in a medical procedure. The sterilization container 12 may include any variety of containers, such as those that are placed within a sterilization machine or autoclave, and/or containers that include internal sterilization mechanisms.

Figure 4:
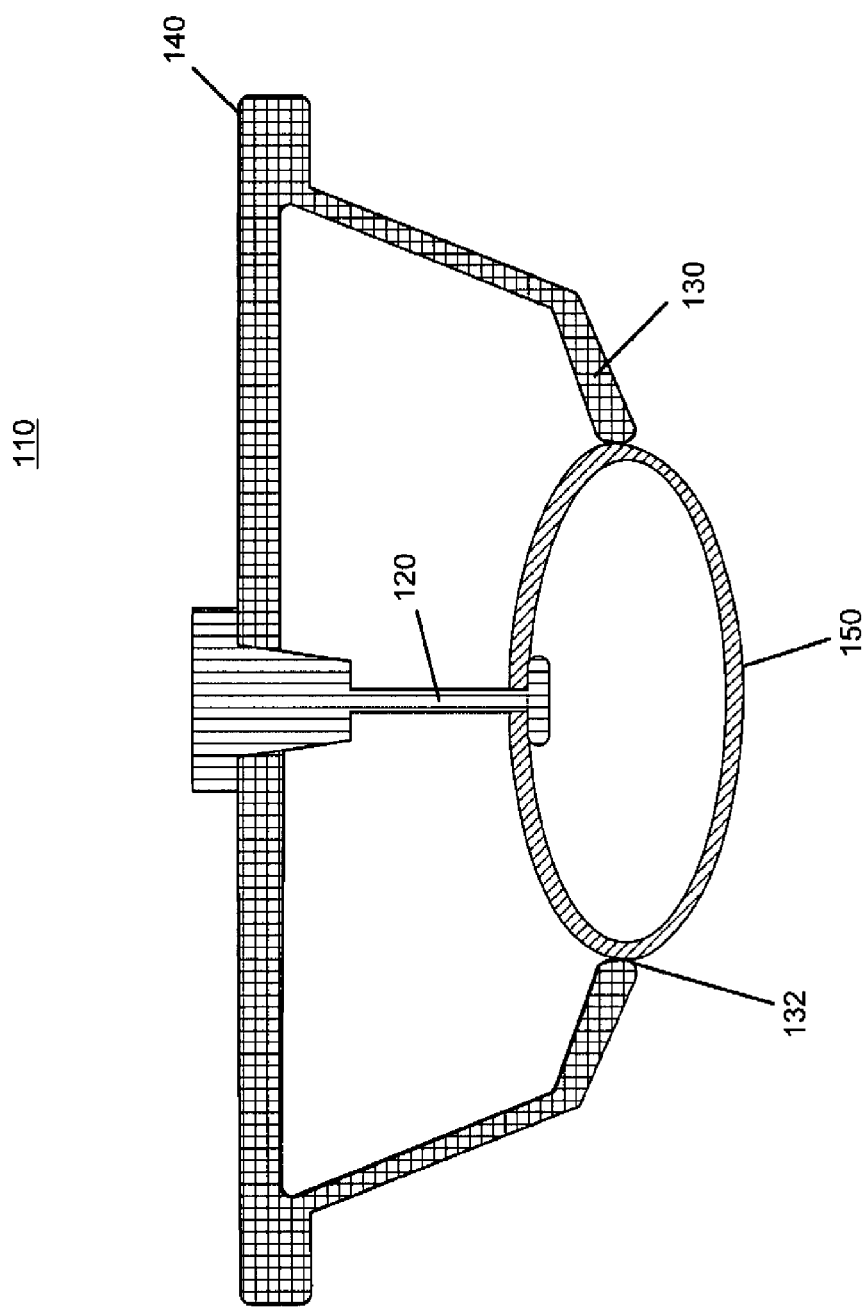
FIG. 4 is a cross-sectional illustration of a valve apparatus, in accordance with a second exemplary embodiment of the present disclosure.

FIG. 4 is a cross-sectional illustration of a valve apparatus, in accordance with a second exemplary embodiment of the present disclosure. The valve apparatus 110, which may be referred to herein as 'apparatus 110' may include any of the features, structures, or configurations disclosed with respect to the first exemplary embodiment. The valve apparatus 110 includes a valve housing structure 140. A first valve portion 130 is connected to the valve housing structure 140, wherein the first valve portion 130 has a sealing edge 132. A second valve portion 120 is positioned at least partially within the valve housing structure 140. A constrictable membrane 150 has a pressurizable interior compartment 129, where the constrictable membrane 150 is supported by the second valve portion 120 and positioned proximate to the first valve portion 130. At least a portion of the constrictable membrane 150 is movable to engageable with the sealing edge 132 of the first valve portion 130.

The valve apparatus 110 may function substantially similar to the valve apparatus 10 of the first exemplary embodiment, in that the constrictable membrane 150 may move between at least a first position where the constrictable membrane 150 engages the sealing edge 132 of the first valve portion 130 to create a seal, and a second position where the constrictable membrane 150 does not contact the sealing edge 132 of the first valve portion 130. However, the valve apparatus 110 differs in that the constrictable membrane 150 may be a sphere or spheroid shape and not stretched over parts of the second valve apparatus 120. The constrictable membrane 150 as a sphere or spheroid shape may decrease and increase in size with the varying pressure and temperature inside an autoclave, and in ambient atmospheric temperatures and pressures. As is shown in FIG. 4, the constrictable membrane 150 is in the closed position such that it contacts the sealing edge 132 of the first valve portion 130. In this position, the constrictable membrane 150 prevents the flow of fluid, gasses, or other materials through the valve apparatus 110.

Figure 5:
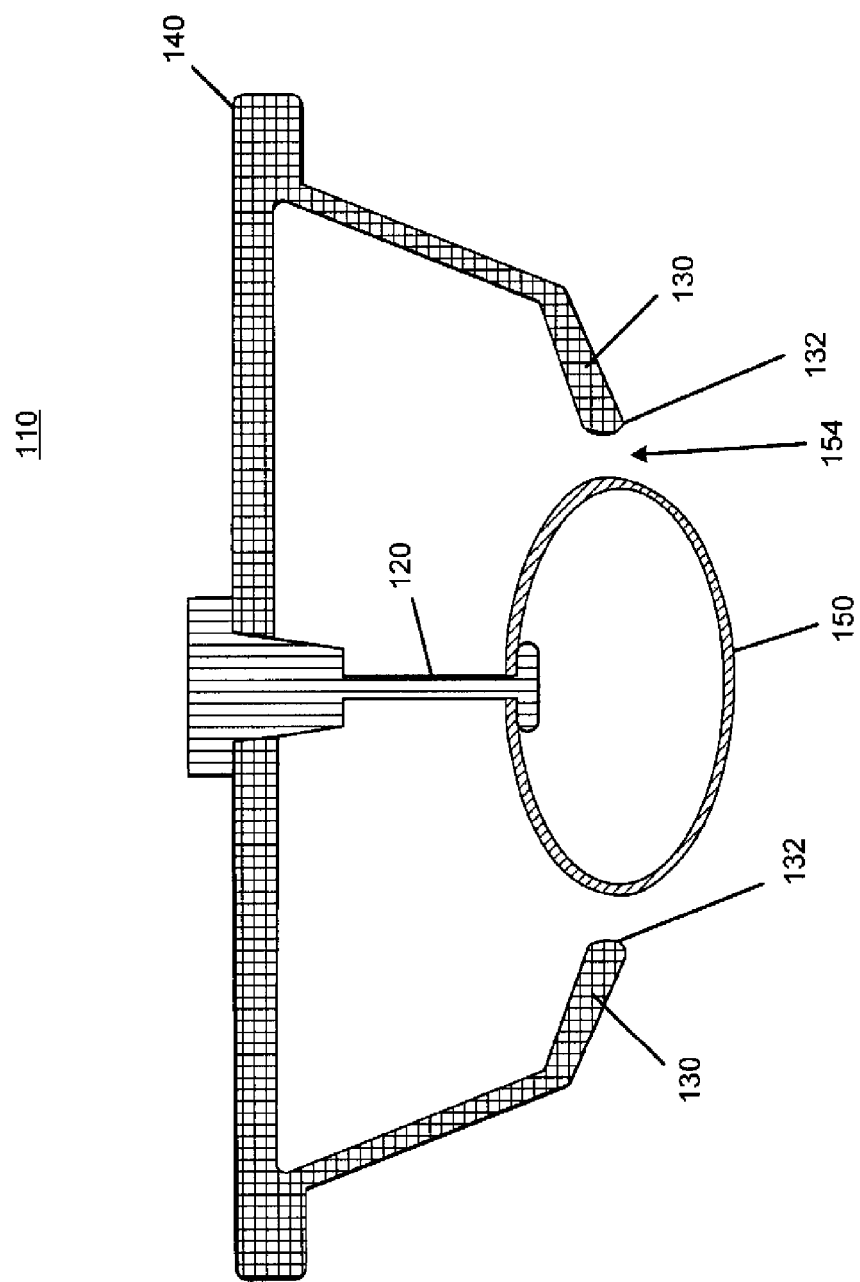
FIG. 5 is a cross-sectional illustration of a valve apparatus of FIG. 4 in a non-engaged position, in accordance with the second exemplary embodiment of the present disclosure.

FIG. 5 is a cross-sectional illustration of a valve apparatus 110 of FIG. 4 in a non-engaged position, in accordance with the second exemplary embodiment of the present disclosure. Compared to FIG. 1, which illustrates the valve apparatus 110 in the closed position, FIG. 5 illustrates the valve apparatus 110 in the open position. With reference to FIGS. 4 and 5, constrictable membrane 150 may be in the non-engaged or non-contacting position when it is positioned to create a void 154 between the constrictable membrane 150 and the first valve portion 130 to allow the flow of gasses and/or sterilant through the valve apparatus 110. The valve apparatus 110 may function by allowing the transmission of a sterilization material, a gas, a liquid and/or a pressurized atmosphere from one side of the valve apparatus 110 to the other side. The void 154 may permit the sterilization material, gas, liquid and/or pressurized atmosphere to traverse through the valve apparatus 110. Thus, the first and second valve portions 130, 120 may remain in substantially constant relative positions to one another while the constrictable membrane 150 is flexed between positions.

Movement between the closed position shown in FIG. 4 and the open position shown in FIG. 5 may occur through the application of pressure to and/or within the sterilization container. Pressure may be applied in any pressurized environment, such as an autoclave chamber used to create pressure and heat for a sterilization process. For example, the sterilization container with valve apparatus 110 may be placed within an autoclave chamber. When the pressure within the autoclave chamber is substantially equal to that outside the autoclave chamber, the constrictable membrane 150 may remain in the closed/engaged position. When the pressure in the autoclave chamber increases, such as from the application of heat in a sterilization process, the constrictable membrane 150 may be forced to move from the closed/engaged position to the open/non-engaged position. This movement of the constrictable membrane 150 is due to the pressure within the interior portion of the second valve portion 120 remaining at an atmospheric pressure of approximately 14.7 psi, while the pressure within the autoclave chamber increases above the atmospheric pressure. For example, the pressure within the autoclave chamber may increase up to approximately 42 psi. Thus, as the pressure within the autoclave chamber is adjusted, the position of the constrictable membrane 150 between a fully closed, fully engaged position with the first valve portion 130 and an open, non-engaged position with the first valve portion 130 may be achieved.

Figure 6:
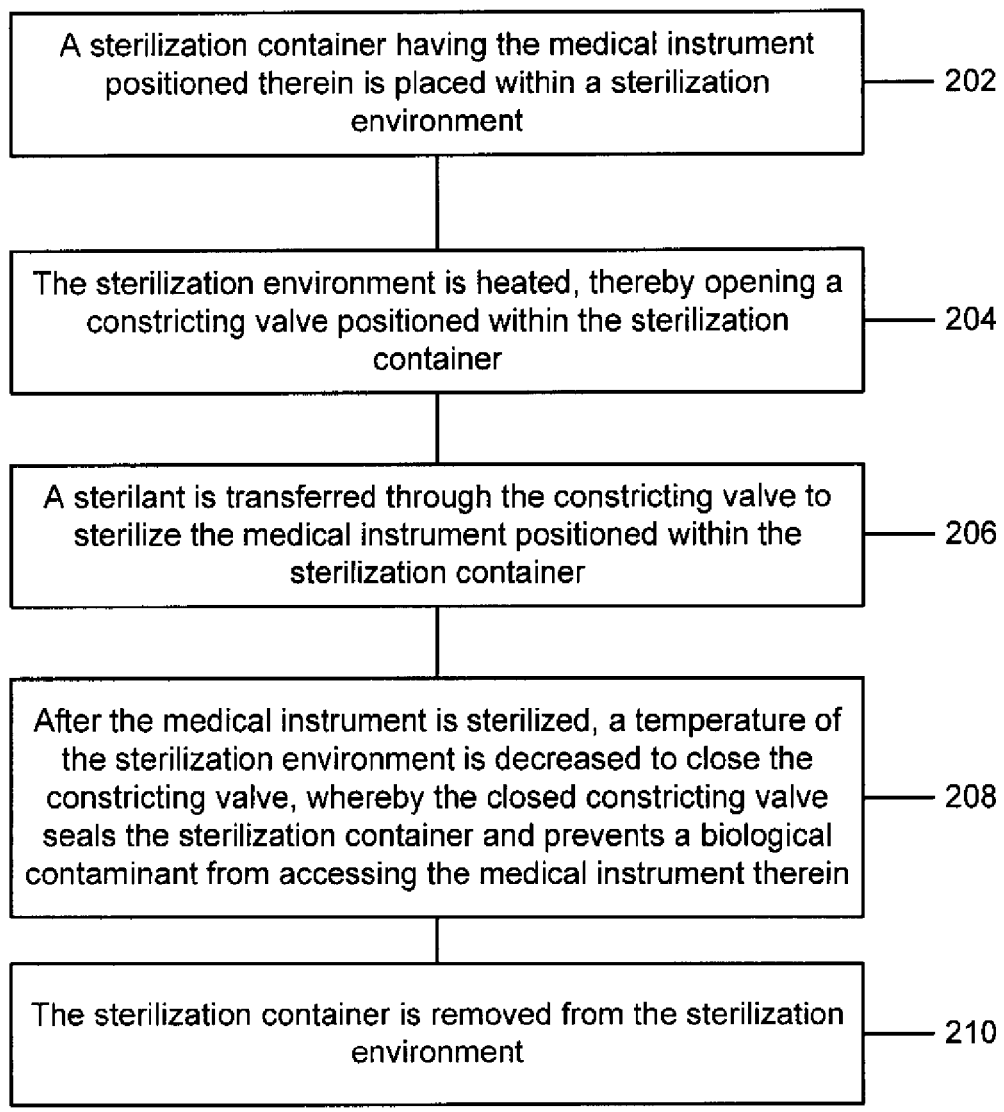
FIG. 6 is a flowchart illustrating a method of sterilizing a medical instrument, in accordance with the first exemplary embodiment of the present disclosure.

FIG. 6 is a flowchart 200 illustrating a method of sterilizing a medical instrument in accordance with the first exemplary embodiment of the disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 202, a sterilization container having the medical instrument positioned therein is placed within a sterilization environment. The sterilization environment is heated, thereby opening a constricting valve positioned within the sterilization container (block 204). A sterilant is transferred through the constricting valve to sterilize the medical instrument positioned within the sterilization container (block 206). After the medical instrument is sterilized, a temperature of the sterilization environment is decreased to close the constricting valve, whereby the closed constricting valve seals the sterilization container and prevents a biological contaminant from accessing the medical instrument therein (block 208). The sterilization container is removed from the sterilization environment (block 210).

The method may include any additional number of steps, variations, or functions, including any steps, variations, or functions disclosed with respect to FIGS. 1-5 above. For example, heating the sterilization container may disengage a constrictable membrane having a pressurizable interior compartment from a sealing edge of a first valve portion affixed to a valve housing structure. Similarly, cooling the sterilization container may engage the constrictable membrane having the pressurizable interior compartment from the sealing edge of the first valve portion affixed to the valve housing structure. The constrictable membrane having the pressurizable interior compartment may remain closed to seal the sterilization container under ambient atmospheric pressures. The sterile conditions within the sterilization container may be maintained for any period of time after it is removed from the sterilization environment.

It should be emphasized that the above-described embodiments of the present disclosure, particularly, any "preferred" embodiments, are merely possible examples of implementations, merely set forth for a clear understanding of the principles of the disclosure. Many variations and modifications, including variations of devices, structures, processes and methods, may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A valve apparatus comprising:
a valve housing structure;
a first valve portion connected to the valve housing structure, wherein the first valve portion has a sealing edge;
a second valve portion positioned at least partially within the valve housing structure, wherein the second valve portion further comprises an upper valve part and a lower valve part having a gap positioned between the upper and lower valve parts; and
a constrictable membrane having a pressurizable interior compartment, the constrictable membrane supported by the second valve portion and positioned proximate to the first valve portion, wherein at least a portion of the constrictable membrane is movable to be engageable with the sealing edge of the first valve portion, wherein the constrictable membrane is affixed between the upper and lower valve parts and across the gap, wherein the sealing edge of the first valve portion is positioned within the gap formed between the upper and lower valve parts, wherein the constrictable membrane is movable between at least a first position where the constrictable membrane engages the sealing edge of the first valve portion to create a seal, and a second position where the constrictable membrane does not contact the sealing edge of the first valve portion.

2. The valve apparatus of claim 1, wherein the valve housing structure is positioned within at least one of a top, a base, and a sidewall of a medical instrument sterilization container.

3. The valve apparatus of claim 1, wherein at least a portion of the constrictable membrane is movable between at least a first position where the constrictable membrane engages the sealing edge of the first valve portion to create a seal, and a second position where the constrictable membrane does not contact the sealing edge of the first valve portion.

4. The valve apparatus of claim 3, wherein when the constrictable membrane is in the first position, movement of a gaseous material through the valve housing structure is restricted.

5. The valve apparatus of claim 3, wherein the second position of the constrictable membrane corresponds to at least one of a high heat and a high pressure condition within a sterilization environment, relative to an ambient heat and an ambient pressure.

6. The valve apparatus of claim 1, wherein the constrictable membrane is stretched over an exterior surface of the second valve portion.

7. The valve apparatus of claim 1, wherein the second valve portion is positioned within the valve housing structure with a threaded fastener.

8. The valve apparatus of claim 1, wherein the upper valve part and the lower valve part are affixed to the valve housing with a threaded fastener.

9. The valve apparatus of claim 1, wherein the sealing edge of the first valve portion is circumferentially positioned about the constrictable membrane.

10. The valve apparatus of claim 1, wherein the constrictable membrane is one of a sphere and a spheroid.

11. A system for sterilizing medical instruments comprising:
- a sterilization container having a plurality of walls, a base, and a top, wherein at least a portion of the plurality of walls, the base, and the top substantially enclose an interior area of the sterilization container;
- a valve housing structure positioned within at least one of the plurality of walls, the base, and the top;
- a first valve portion connected to the valve housing structure, wherein the first valve portion has a sealing edge;
- a second valve portion positioned at least partially within the valve housing structure, wherein the second valve portion further comprises an upper valve part and a lower valve part having a gap positioned between the upper and lower valve parts; and
- a constrictable membrane having a pressurizable interior compartment, the constrictable membrane supported by the second valve portion and positioned proximate to the first valve portion, wherein the constrictable membrane is affixed between the upper and lower valve parts and across the gap, wherein the sealing edge of the first valve portion is positioned within the gap formed between the upper and lower valve parts, wherein the constrictable membrane is movable between at least a first position where the constrictable membrane engages the sealing edge of the first valve portion to create a seal, and a second position where the constrictable membrane does not contact the sealing edge of the first valve portion.

12. The system for sterilizing medical instruments of claim 11, wherein in the first position where the constrictable membrane engages the sealing edge of the first valve portion to seal an interior area of the sterilization container from an exterior atmosphere, and in the second position the constrictable membrane does not contact the sealing edge of the first valve portion to provide a pathway through the valve housing structure between the interior area of the sterilization container and the exterior atmosphere.

* * * * *